(12) United States Patent  (10) Patent No.: US 9,122,063 B2
Huang  (45) Date of Patent: Sep. 1, 2015

(54) VIRTUAL IMAGE DISPLAYING SYSTEM (71) Applicant: DELTA ELECTRONICS, INC., Taoyuan Hsien (TW)

(72) Inventor: Junejei Huang, Taoyuan Hsien (TW)

(73) Assignee: DELTA ELECTRONICS, INC., Taoyuan Hsien (TW)

( * ) Notice: Subject to any disclaimer, the term of this patent is extended or adjusted under 35 U.S.C. 154(b) by 378 days.

(21) Appl. No.: 13/859,289

(22) Filed: Apr. 9, 2013

(65) Prior Publication Data

US 2014/0184932 A1  Jul. 3, 2014

(30) Foreign Application Priority Data

Dec. 28, 2012 (TW) ............................. 101150748 A (51) Int. Cl.
*G03B 21/00* (2006.01)
*G02B 27/22* (2006.01)
*A61B 5/00* (2006.01)

(52) U.S. Cl.
CPC ............ *G02B 27/22* (2013.01); *G02B 27/2235* (2013.01); *A61B 5/742* (2013.01)

(58) Field of Classification Search
CPC .................................................. G02B 27/2292
USPC ....................................................... 353/7–10
See application file for complete search history.

(56) References Cited

U.S. PATENT DOCUMENTS

| 5,865,519 | A | * | 2/1999 | Maass | ............................. 353/28 |
| 6,552,760 | B1 | | 4/2003 | Gotoh et al. | |
| 6,877,860 | B2 | | 4/2005 | Cho et al. | |
| 7,237,908 | B2 | | 7/2007 | Suzuki et al. | |
| 7,341,353 | B2 | | 3/2008 | Peterson et al. | |
| 7,646,540 | B2 | | 1/2010 | Dolgoff | |
| 7,722,189 | B2 | | 5/2010 | Miles | |
| 2008/0285127 | A1 | * | 11/2008 | Ochi | ............................. 359/462 |
| 2011/0285968 | A1 | | 11/2011 | Huang | |
| 2012/0140182 | A1 | | 6/2012 | Relke et al. | |
| 2012/0147333 | A1 | | 6/2012 | Jorgensen | |

* cited by examiner

*Primary Examiner* — Sultan Chowdhury
*Assistant Examiner* — Danell L Owens
(74) *Attorney, Agent, or Firm* — Grossman, Tucker, Perreault & Pfleger, PLLC (57) ABSTRACT

A virtual image displaying system is disclosed and includes: a projector, an optical relaying device, a reflective mirror and a slit array. The projector has a main body and a projection lens connecting to the main body. The main body outputs a light beam by the projection lens. The optical relaying device faces the projection lens and is disposed under the projection lens. The reflective mirror is inclined relative to and disposed above the optical relaying device. The slit array is inclined relative to and disposed in front of the reflective mirror. The projection lens is further disposed between the reflective mirror and the slit array. Therefore, the virtual image displaying system has a compact configuration of components.

8 Claims, 11 Drawing Sheets

VIRTUAL IMAGE DISPLAYING SYSTEM

CROSS-REFERENCES TO RELATED APPLICATIONS

This application claims priority to Taiwan Patent Application No. 101150748 filed on Dec. 28, 2012, which is hereby incorporated herein by reference in its entirety.

BACKGROUND OF THE INVENTION

1. Field of the Invention

The present invention provides a displaying system, and more particularly, to a virtual image displaying system.

2. Descriptions of the Related Art

Over recent years, stereoscopic image displays have become a hot topic in research. The primary principle of stereoscopic image displays is as follows: a left-eye view-angle image and a right-eye view-angle image are fed by a display apparatus to the left eye and the right eye of a viewer respectively. Then, when the two images with the same image content but different parallaxes are viewed by both eyes of the viewer, depth will be perceived in the resulting image by the viewer because of the visual characteristics of the human eye. Thus, the resulting image is perceived as a stereoscopic image.

There are many technologies that can accomplish the aforesaid stereoscopic displaying principle, one of which is termed as the "time-multiplex autostereoscopic displaying system."

Figure 9:
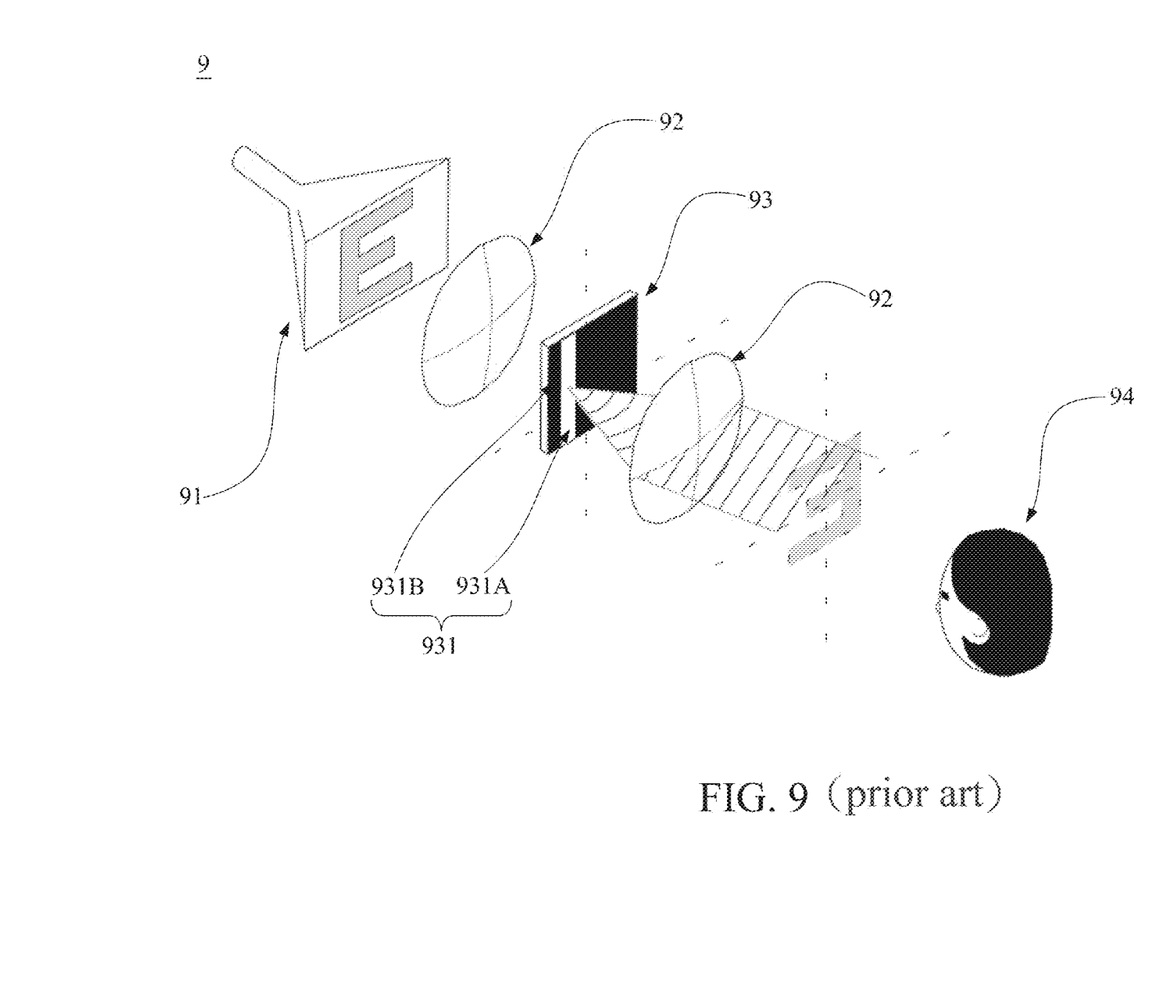
FIG. 9 is a schematic view of a conventional virtual image displaying system.

With reference to FIG. 9, the so-called "time-multiplex autostereoscopic displaying system" was invented by Professor Adrian Travis of Cambridge University. The displaying system 9 has a cathode ray tube (CRT) display 91, two lenses 92 and a shutter or slit array 93.

The CRT 91 can project a light beam (i.e., an image), which then propagates through the lenses 92 to impinge on the slit array 93. The slit array 93 has a plurality of slits 931 which can be turned on sequentially rather than simultaneously. More specifically, at a certain time point, only one slit 931A among the slits 931 is turned on while the other slits 931B are all turned off.

Although the light beam impinges on all the slits 931 of the slit array 93, only a small part of the light beam can pass through the only slit 931A that is turned on while other parts of the light beam are blocked by the slits 931B that are turned off. The CRT 91 can adjust the intensity of the light beam projected by each pixel thereof (i.e., the CRT 91 can adjust the image displayed) according to the position of the slit 931A that is turned on. Therefore, as the slits 93 are turned on in sequence, each pixel of the CRT 91 will emit a light beam of different intensities and in different directions from the slit array 93.

By emitting light beams of different intensities and in different directions, the displaying system 9 can simulate light rays emitted by an object in a space to form a virtual image of the object that can be viewed by a viewer 94 in front of the slit array 93. In this sense, the time-multiplex autostereoscopic displaying system may also be termed as a "virtual image displaying system."

The virtual image displaying system may be used in medical applications to allow medical workers to view stereoscopic images of patients' organs by means of the displaying system. The virtual image displaying system may also be used in a video call to allow both parties of the call to see each other's stereoscopic images.

However, the conventional virtual image displaying system has a bulky volume and occupies a large space, so the location where it is placed is limited and this makes it difficult to place it directly onto a desktop. Furthermore, if a large-size displaying frame is desired, the volume of the conventional virtual image displaying system must be increased significantly. For this reason, the conventional virtual image displaying system can only provide small-size displaying frames.

Accordingly, there is a need existed in the art to provide a virtual image displaying system that can overcome at least one of the aforesaid shortcomings.

SUMMARY OF THE INVENTION

An objective of the present invention is to provide a virtual image displaying system, which allows components thereof to be arranged in a compact manner.

Another objective of the present invention is to provide a virtual image displaying system which can provide a large-size displaying frame.

To achieve the aforesaid objectives, a virtual image displaying system disclosed in the present invention comprises the following: a projector, including a main body and a projection lens which is connected to the main body, wherein the main body is used to output a light beam by the projection lens; an optical relaying structure, facing the projection lens and disposed under the projection lens; a reflective mirror, being inclined relative to the optical relaying structure and disposed above the optical relaying structure; and a slit array, being inclined relative to the reflective mirror and disposed in front of the reflective mirror, wherein the slit array has a plurality of slits; wherein the projection lens is disposed in an interval between the reflective mirror and the slit array.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1A:
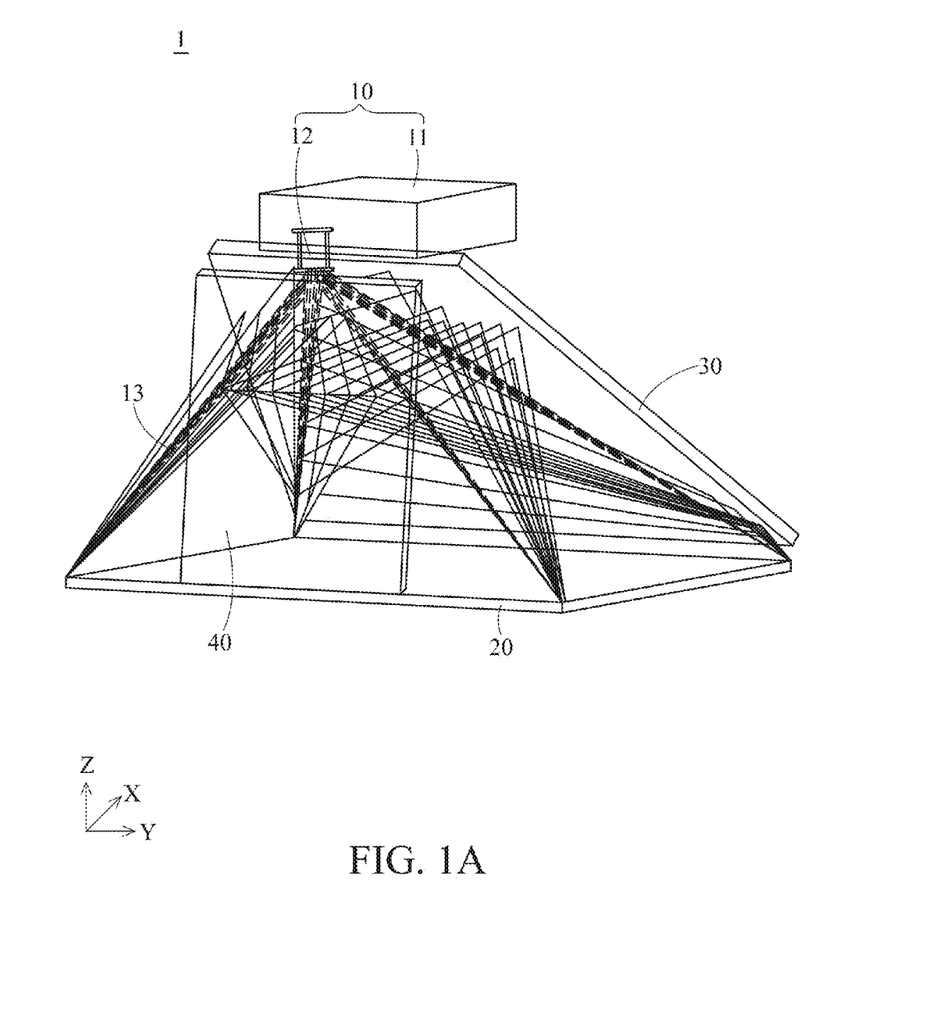
FIG. 1A is a schematic perspective view of a virtual image displaying system according to the first preferred embodiment of the present invention (with light beams shown)
Figure 1B:
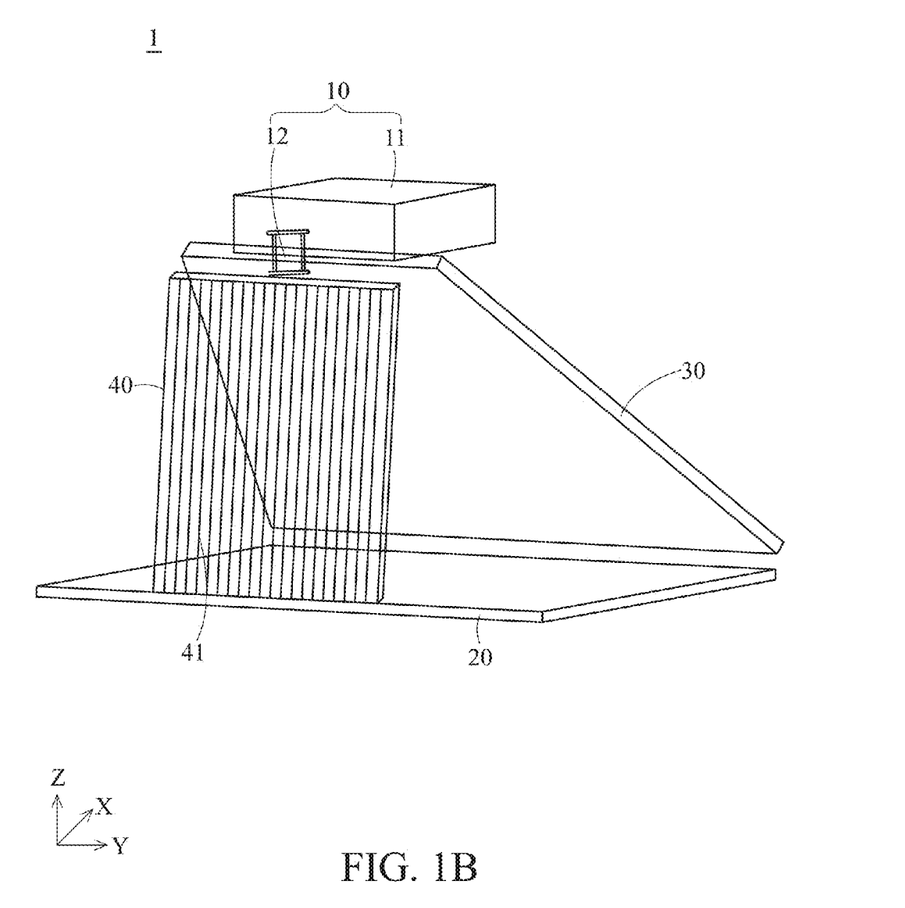
FIG. 1B is another schematic perspective view of the virtual image displaying system according to the first preferred embodiment of the present invention (with light beams not shown)
Figure 2:
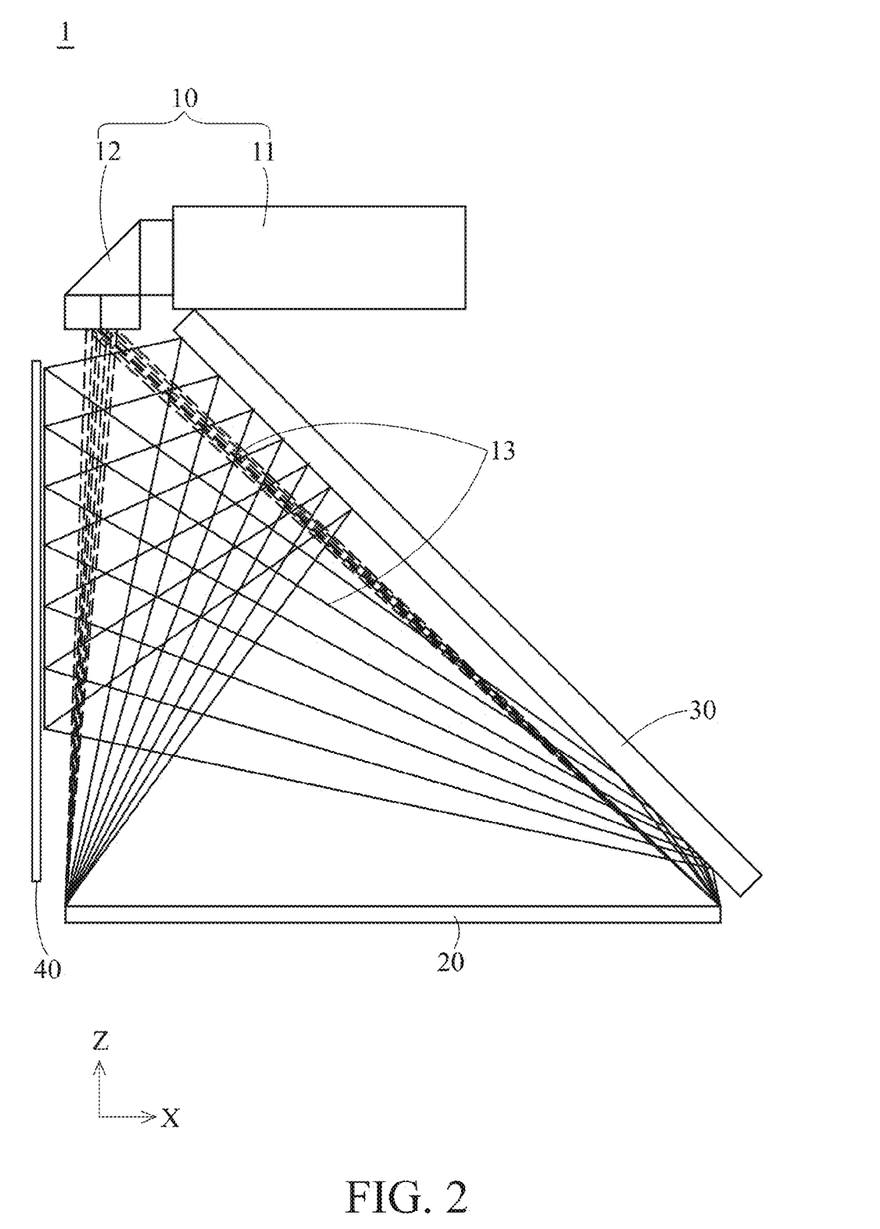
FIG. 2 is a schematic plan view (side view) of the virtual image displaying system according to the first preferred embodiment of the present invention.
Figure 3:
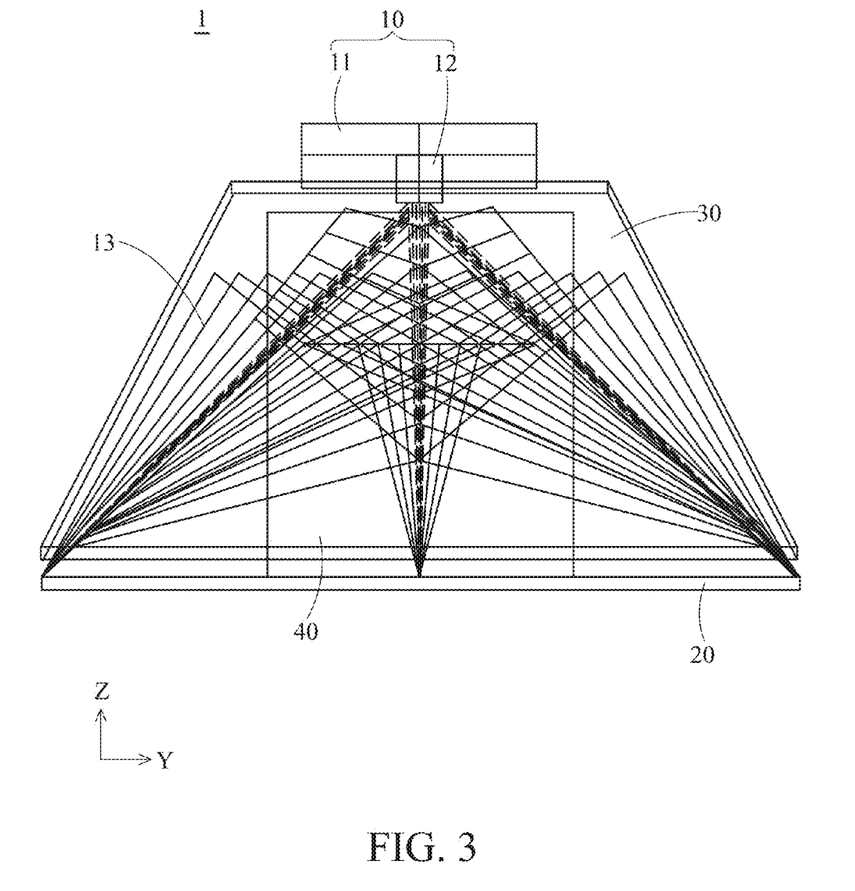
FIG. 3 is another schematic plan view (front view) of the virtual image displaying system according to the first preferred embodiment of the present invention.

FIGS. 1A and 1B show two schematic perspective views of a virtual image displaying system according to the first preferred embodiment of the present invention respectively. FIGS. 2 and 3 show two schematic plan views of the virtual image displaying system according to the first preferred embodiment of the present invention respectively.

In the first embodiment of the present invention, a virtual image displaying system 1 is proposed. The virtual image displaying system 1 is disposed in a space which has a first direction X, a second direction Y and a third direction Z that are perpendicular to one another. The first direction X and the second direction Y may be horizontal directions, while the third direction Z may be a vertical direction.

The virtual image displaying system 1 comprises a projector 10, an optical relaying structure 20, a reflective mirror 30 and a slit array 40. The technical contents of these components will be described sequentially as follows.

The projector 10 has a main body 11 and a projection lens 12 which is connected to the main body 11. As a major part of the projector 10, the main body 11 comprises primary components such as a light source and an imaging device (e.g., DMD). The main body 11 can produce a light beam (i.e., an image) 13 propagating to the projection lens 12 which then outputs the light beam 13. In other words, the main body 11 can output the light beam 13 by means of the projection lens 12.

In this embodiment, the projection lens 12 may be a wide-angle lens, which outputs the light beam 13 with a large diffusing angle so that the light beam 13 can impinge everywhere on the optical relaying structure 20. However, if the optical relaying structure 20 has a small area, the projection lens 12 does not need to have a wide-angle lens.

In this embodiment, the main body 11 is disposed horizontally (i.e., disposed in the first direction X). In order for the light beam 13 produced by the main body 11 to be outputted downwards, the projection lens 12 is implemented to redirect the light beam 13, such as an L-shaped projection lens. If the main body 11 is disposed vertically (i.e., disposed in the third direction Z, not shown), the projection lens 12 is not required to be implemented as an L-shaped projection lens.

The optical relaying structure 20 faces the projection lens 12 and is disposed under the projection lens 12 so that the light beam 13 outputted by the projection lens 12 can impinge on the optical relaying structure 20. After impinging on the optical relaying structure 20, the light beam 13 is then relayed by the optical relaying structure 20 to the reflective mirror 30.

Figure 4:
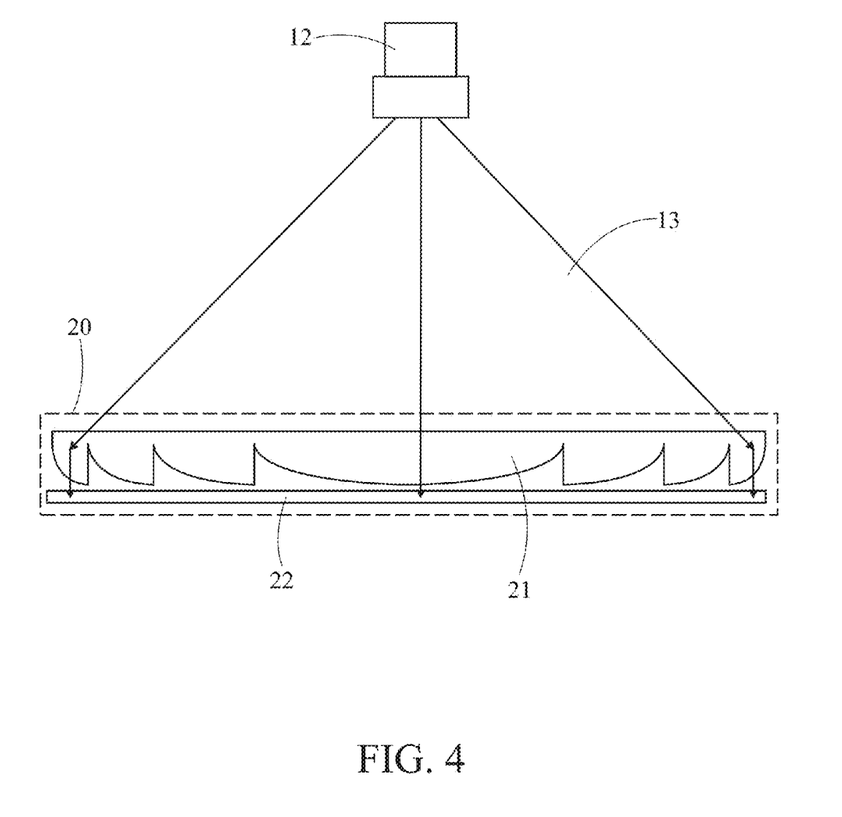
FIG. 4 is a schematic plan view (front view) of a projection lens and an optical relaying structure of the virtual image displaying system according to the first preferred embodiment of the present invention.

FIG. 4 is a schematic plan view (front view) of the projection lens and the optical relaying structure of the virtual image displaying system of the first preferred embodiment of the present invention. The optical relaying structure 20 may be implemented by a lens, a diffuser plate, a reflective mirror and the like, and in this embodiment, is implemented to have a Fresnel lens 21 and a diffuser plate 22 which is disposed under the Fresnel lens 21.

When the light beam 13 impinges on the optical relaying structure 20, it will be first collected to the diffuser plate 22 by the Fresnel lens 21, and then diffused in the diffuser plate 22. The diffuser plate 22 itself may be a diffusing reflective layer (not shown) with microstructures. A reflective mirror (not shown) may also be disposed under the diffuser 22 to reflect the diffused light beam 13 back to the Fresnel lens 21. Subsequently, the light beam 13 from projection 12 is imaged to the plane of slit array 40 by passing the Fresnel lens 21 twice and with one bounce at the reflective mirror 30.

With reference to FIGS. 1A to 3, the reflective mirror 30 is inclined relative to the optical relaying structure 20 and disposed above the optical relaying structure 20. The reflective mirror 30 may be disposed behind the projection lens 12. The light beam 13 coming from the optical relaying structure 20 can be reflected by the reflective mirror 30 to the slit array 40.

It shall be appreciated that the shape of the reflective mirror 30 only needs to conform to an irradiation range of the light beam 13 to achieve the purpose of reflecting the light beam 13. In this embodiment, when the light beam 13 coming from the optical relaying structure 20 is projected onto the reflective mirror 30, the light beam 13 generally has a trapezoidal irradiation range (as shown in FIG. 3), so the reflective mirror 30 in this embodiment is preferably implemented as a trapezoid-shaped reflective mirror.

The slit array 40 is inclined relative to the reflective mirrors 30 and may be disposed in front of the reflective mirrors 30. There is an interval between the slit array 40 and the reflective mirror 30 in the first direction X; the projection lens 12 is disposed in this interval. In general, the slit array 40, the projection lens 12 and the reflective mirror 30 are arranged sequentially in the first direction X.

The slit array 40 has a plurality of slits 41 (as shown in FIG. 1B) and, in this embodiment, has one hundred (i.e. 100) slits 41. Each of the slits 41 can be turned on by using electrical power to allow different parts of the light beam 13 coming from the reflective mirror 30 to pass therethrough. Furthermore, the slits 41 are turned on sequentially rather than simultaneously. In other words, only one slit 41 among the one hundred slits 41 is turned on at a time, while other slits 41 are all turned off. In this way, at a certain time point, only a small part of the light beam 13 will pass through the slit 41 that is turned on and be viewed by a viewer. After the slits 41 are turned on sequentially by a round, a virtual image is created.

The slit array 40 is preferably a liquid crystal display, with each of the slits 41 comprising one row of liquid crystals in the liquid crystal display. When electric power is applied to the row of liquid crystals, light rays pass therethrough, thereby fulfilling the function of the slit array 41.

Figure 5A:
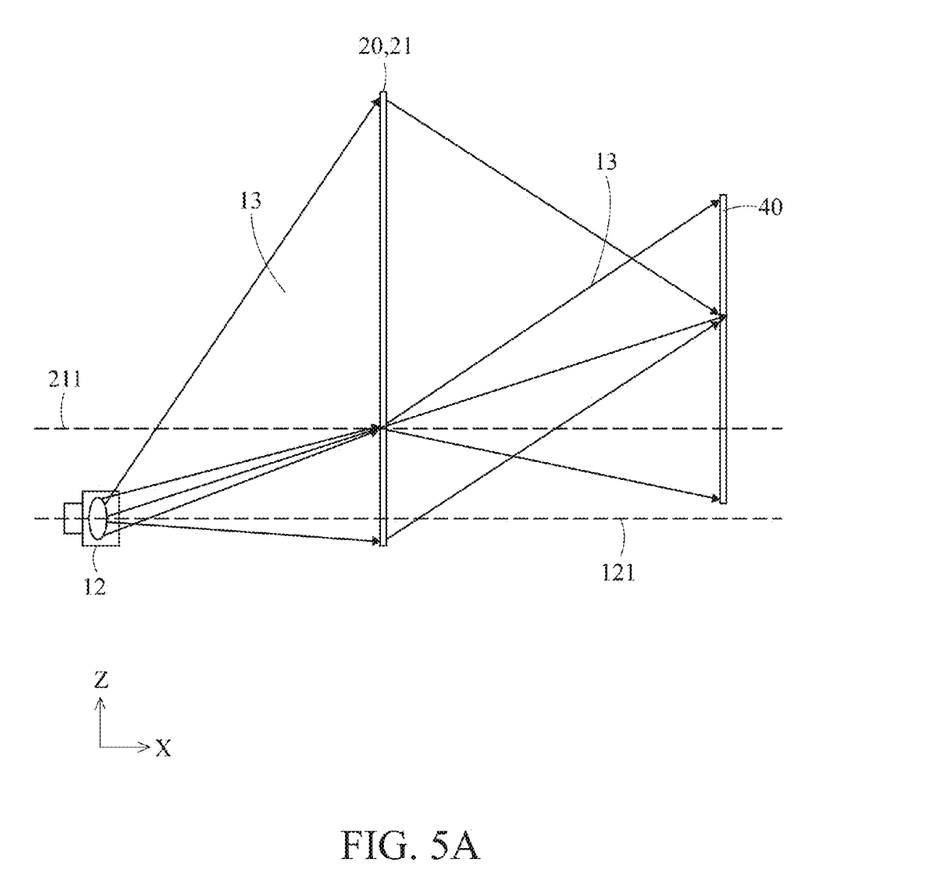
FIG. 5A is a schematic diagram illustrating the unfolding optical path from side view direction of the virtual image displaying system according to the first preferred embodiment of the present invention.

FIG. 5A is a schematic diagram illustrating the unfolding optical path from the side view direction of the virtual image displaying system according to the first preferred embodiment of the present invention. FIG. 5A is obtained by spreading out the light beams propagating among the projection lens 12, the optical relaying structure 20 and the slit array 40 to a plane formed by the first direction X and the third direction Z.

As can be seen from FIG. 5A, an optical axis 211 of the Fresnel lens 21 is not located at the center of the Fresnel lens 21 in the first direction X and is offset from an optical axis 121 of the projection lens 12. Thus, when the light beam 13 is outputted from the projection lens 12 to the Fresnel lens 21 at a location that is offset from the center of the Fresnel lens 21 in the first direction X, the Fresnel lens 21 (the optical relaying structure 20) can still relay the light beam 13 to the slit array 40.

Figure 5B:
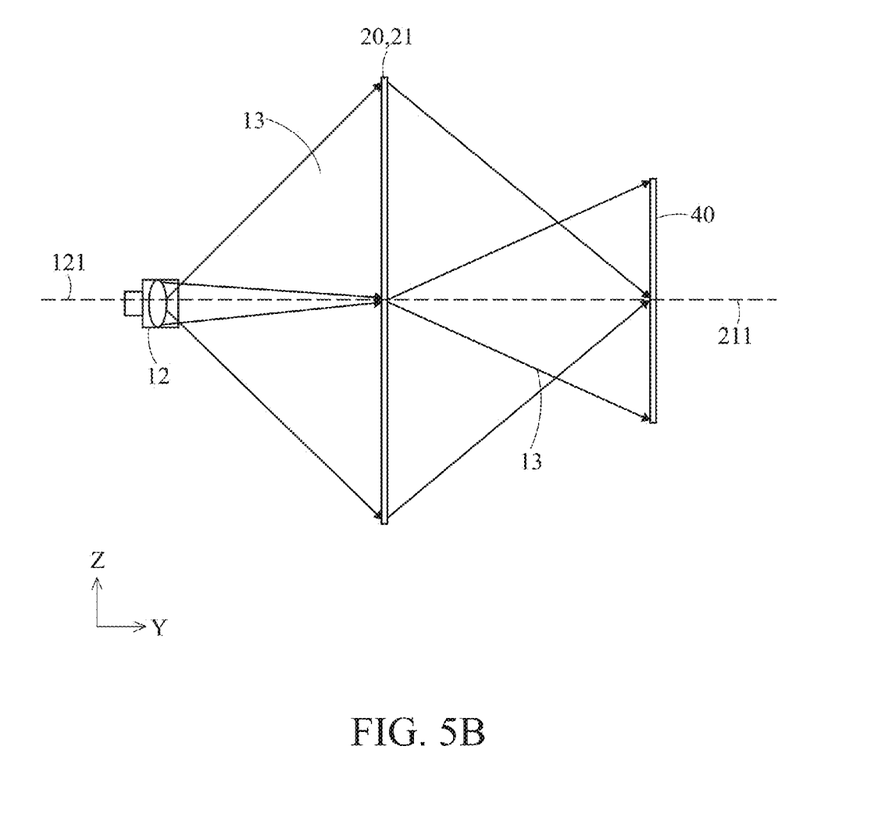
FIG. 5B is a schematic diagram illustrating the unfolding optical path from front view direction of the virtual image displaying system according to the first preferred embodiment of the present invention.

FIG. 5B is a schematic diagram illustrating the unfolding optical path from the front view direction of the virtual image displaying system according to the first preferred embodiment of the present invention. FIG. 5B is obtained by spreading out the light beams propagating among the projection lens 12, the optical relaying structure 20 and the slit array 40 to a plane formed by the second direction Y and the third direction Z.

As can be seen from FIG. 5B, the optical axis 211 of the Fresnel lens 21 may be located at the center of the Fresnel lens 21 in the second direction Y and aligned with the optical axis 121 of the projection lens 21. Thus, the light beam 13 outputted from the projection lens 12 can be relayed by the Fresnel lens 21 (the optical relaying structure 20) to the slit array 40 in the second direction Y.

Figure 6:
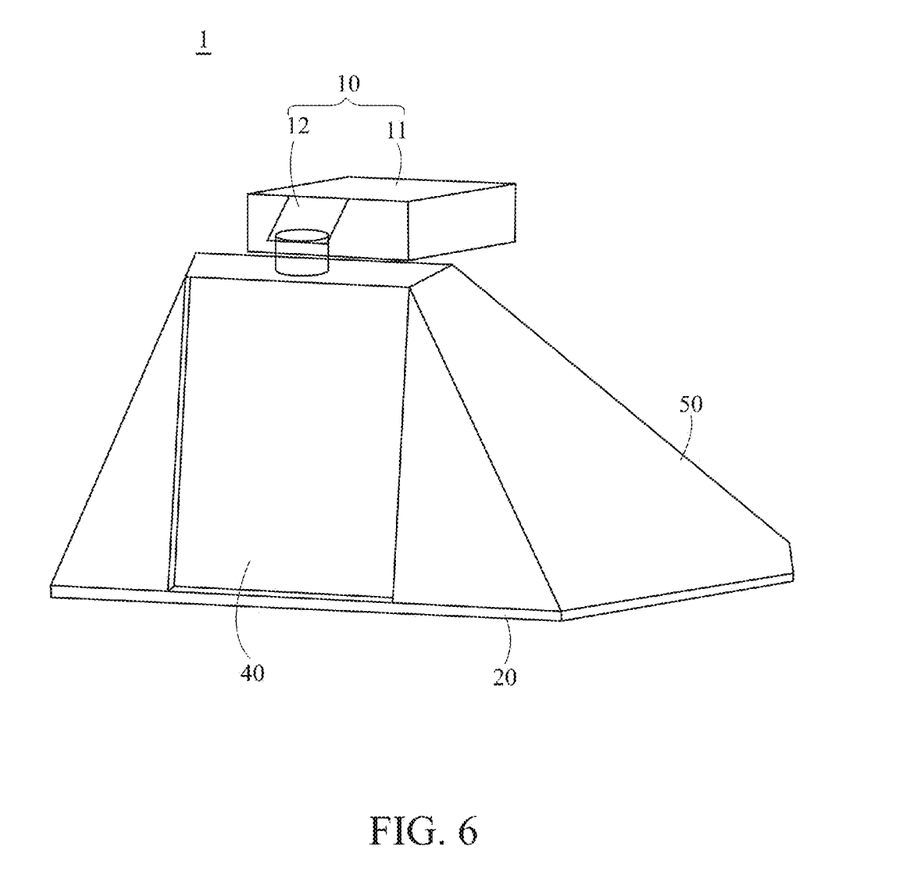
FIG. 6 is a further schematic perspective view of the virtual image displaying system according to the first preferred embodiment of the present invention.

FIG. 6 is a further schematic perspective view of the virtual image displaying system according to the first preferred embodiment of the present invention. The virtual image displaying system 1 of this embodiment may further comprise a housing 50 which may house the projector 10, the optical relaying structure 20 and the reflective mirror 30 partially or entirely.

According to the above descriptions, the virtual image displaying system 1 of this embodiment allows components thereof (i.e., the projector 10, the optical relaying structure 20, the reflective mirror 30 and the slit array 40) to be arranged in a compact manner, which can reduce the overall volume of the virtual image displaying system 1. Also, with such an arrangement of components, "a light path from the projection lens 12 to the optical relaying structure 20" and "a light path from the optical relaying structure 20 to the slit array 40" are located in the same space (i.e., a space surrounded by the optical relaying structure 20, the reflective mirror 30 and the slit array 40), and this reduces the space used for propagation of the light beam 13.

Figure 7:
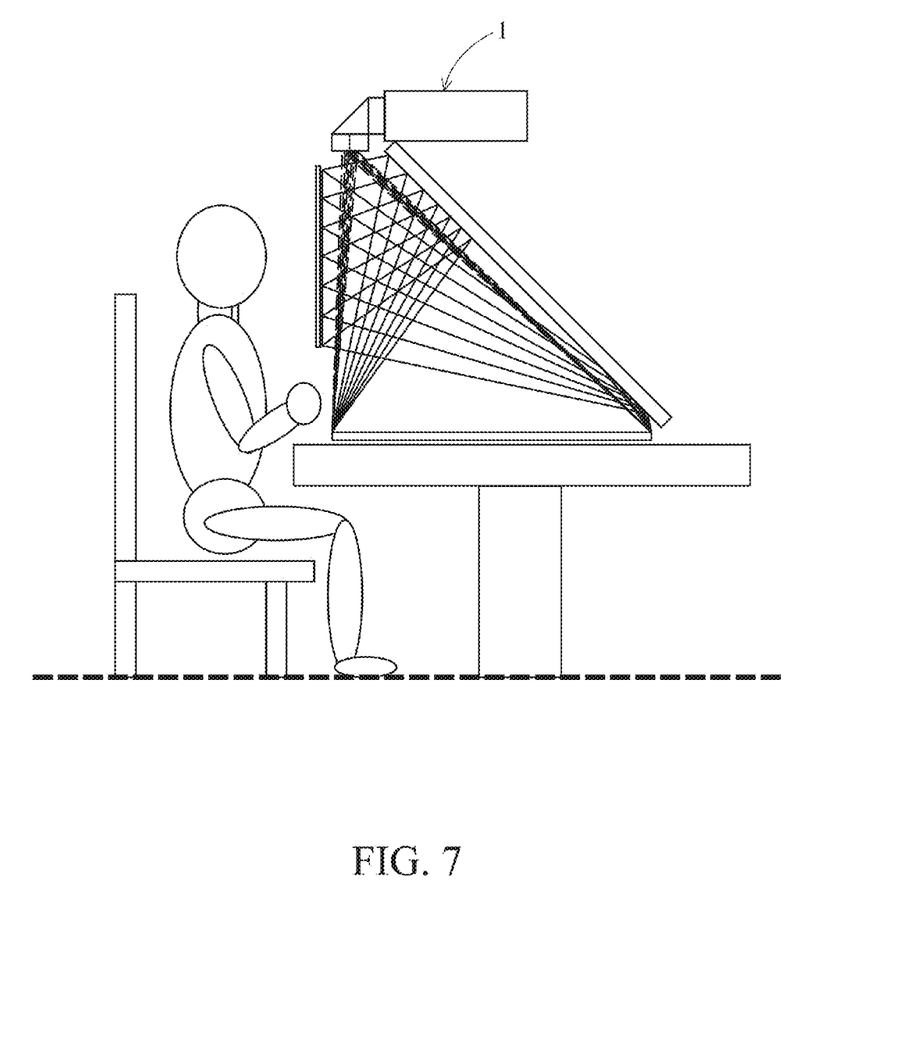
FIG. 7 is a schematic view illustrating the usage state of the virtual image displaying system according to the first preferred embodiment of the present invention.

FIG. 7 is a schematic view illustrating the usage state of the virtual image displaying system according to the first preferred embodiment of the present invention. Since the virtual image displaying system 1 has a smaller volume than the conventional virtual image displaying system, the location where it is placed is not limited and it can also be easily placed onto a desktop.

Figure 8:
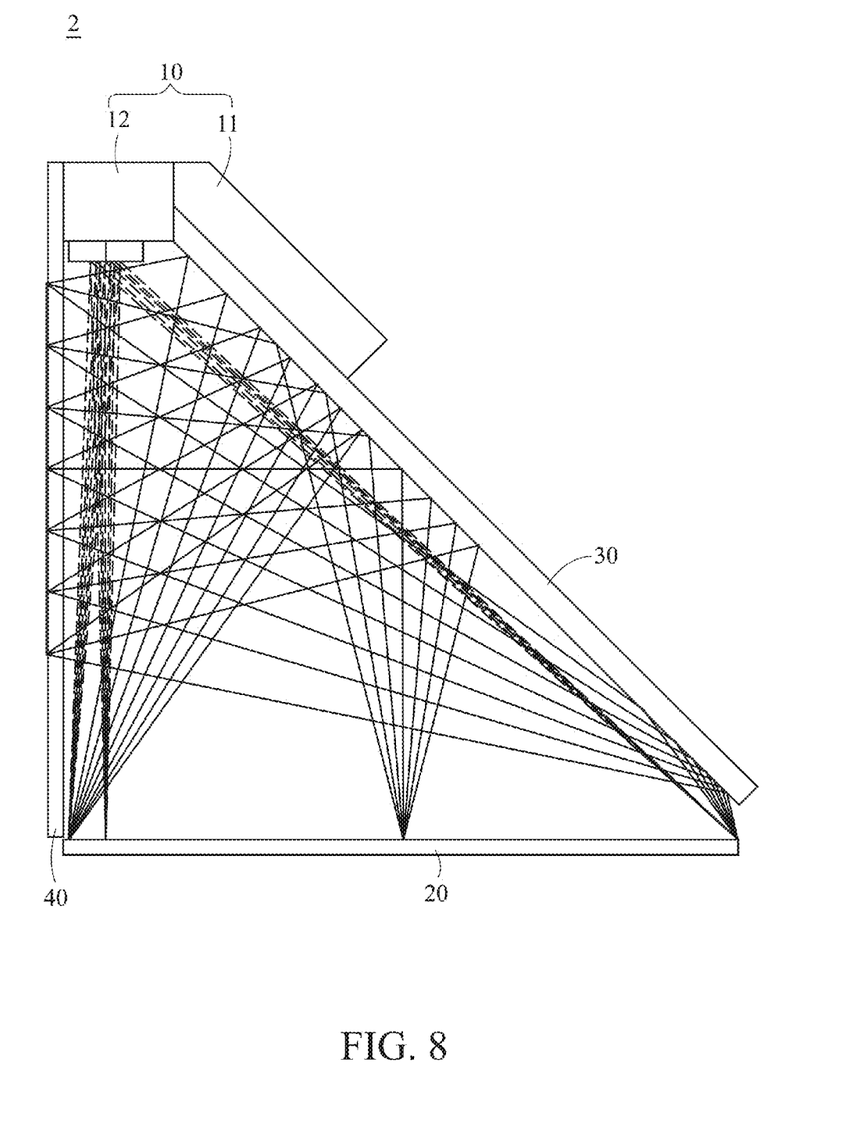
FIG. 8 is a schematic plan view (side view) of a virtual image displaying system according to the second preferred embodiment of the present invention.

FIG. 8 is a schematic plan view of a virtual image displaying system according to the second preferred embodiment of the present invention. In the second embodiment, another virtual image displaying system 2 is proposed. The virtual image displaying system 2 is generally identical to the virtual image displaying system 1 but is different from the virtual image displaying system 1 in that the main body 11 of a projector 10 of the virtual image displaying system 2 is inclined relative to an optical relaying structure 20 as with the reflective mirror 30. An inclining angle of the main body 11 may be identical to that of the reflective mirror 30. By disposing the main body 11 of the projector 10 to be inclined, the overall volume of the virtual image displaying system 2 can be further reduced. Other technical features and effects of the virtual image displaying system 2 are identical or similar to those of the virtual image displaying system 1 and, thus, will not be described again herein.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A virtual image displaying system, comprising:
a projector, including a main body and a projection lens which is connected to the main body, wherein the main body is used to output a light beam by the projection lens;
an optical relaying structure, facing the projection lens and disposed under the projection lens;
a reflective mirror, being inclined relative to the optical relaying structure and disposed above the optical relaying structure; and
a slit array, being inclined relative to the reflective mirror and disposed in front of the reflective mirror, wherein the slit array has a plurality of slits;
wherein, the projection lens is disposed in an interval between the reflective mirror and the slit array.

2. The virtual image displaying system of claim 1, wherein the optical relaying structure includes a Fresnel lens and a diffusing plate which is disposed under the Fresnel lens.

3. The virtual image displaying system of claim 2, wherein an optical axis of the Fresnel lens is offset from an optical axis of the projection lens in a first direction; the optical axis of the Fresnel lens is aligned with the optical axis of the projection lens in a second direction; the first direction and the second direction are perpendicular to each other; the slit array, the projection lens and the reflective mirror are arranged sequentially along the first direction.

4. The virtual image displaying system of claim 1, wherein the main body of the projector is inclined relative to the optical relaying structure.

5. The virtual image displaying system of claim 1, wherein the slit array is a liquid crystal display, and each of the slits is one row of liquid crystals.

6. The virtual image displaying system of claim 1, wherein the reflective mirror is a trapezoid-shaped reflective mirror.

7. The virtual image displaying system of claim 1, wherein the projection lens is an L-shaped projection lens.

8. The virtual image displaying system of claim 1, further comprising a housing which houses the projector, the optical relaying structure and the reflective mirror.

* * * * *